United States Patent [19]
Kent

[11] 4,389,414
[45] Jun. 21, 1983

[54] PROSTAGLANDIN COMPOSITIONS
[75] Inventor: John S. Kent, Cupertino, Calif.
[73] Assignee: Syntex (U.S.A.) Inc., Palo Alto, Calif.
[21] Appl. No.: 262,102
[22] Filed: May 11, 1981

Related U.S. Application Data
[63] Continuation of Ser. No. 75,912, Jul. 16, 1979, abandoned.

[51] Int. Cl.³ ............................................. A61K 31/235
[52] U.S. Cl. .................................................... 424/308
[58] Field of Search .................... 424/305, 308; 560/61

[56] References Cited
U.S. PATENT DOCUMENTS

| | | | |
|---|---|---|---|
| 3,749,800 | 7/1973 | Stehle et al. | 424/318 |
| 3,882,241 | 5/1975 | Pharriss | 424/318 X |
| 3,899,587 | 8/1975 | Phariss | 424/305 |
| 3,985,791 | 10/1976 | Muchowski et al. | 560/61 |
| 4,011,313 | 3/1977 | Thompson | 424/227 |

Primary Examiner—Ethel G. Love
Attorney, Agent, or Firm—James M. Kanagy; Tom M. Moran

[57] ABSTRACT

The mixture of polyethylene glycol having a molecular weight of about 380 to about 630 with the prostaglandins dl-9α,11α,15α-trihydroxy-16-phenoxy-17,18,19,20-tetranorprosta-4,5,13-trans-trieneoic acid and the lower alkyl esters thereof are useful for parenteral administration to mammals as luteolytic agent, primarily for inducing abortion.

6 Claims, 1 Drawing Figure

KEY:
COMPOUND OF FORMULA
I(R=H) IN:
■ ISOTONIC BUFFER, I.M.
● PEG 400, S.Q.
▽ 100% GLYCERIN, S.Q.
✕ 90% GLYCERIN, S.Q.

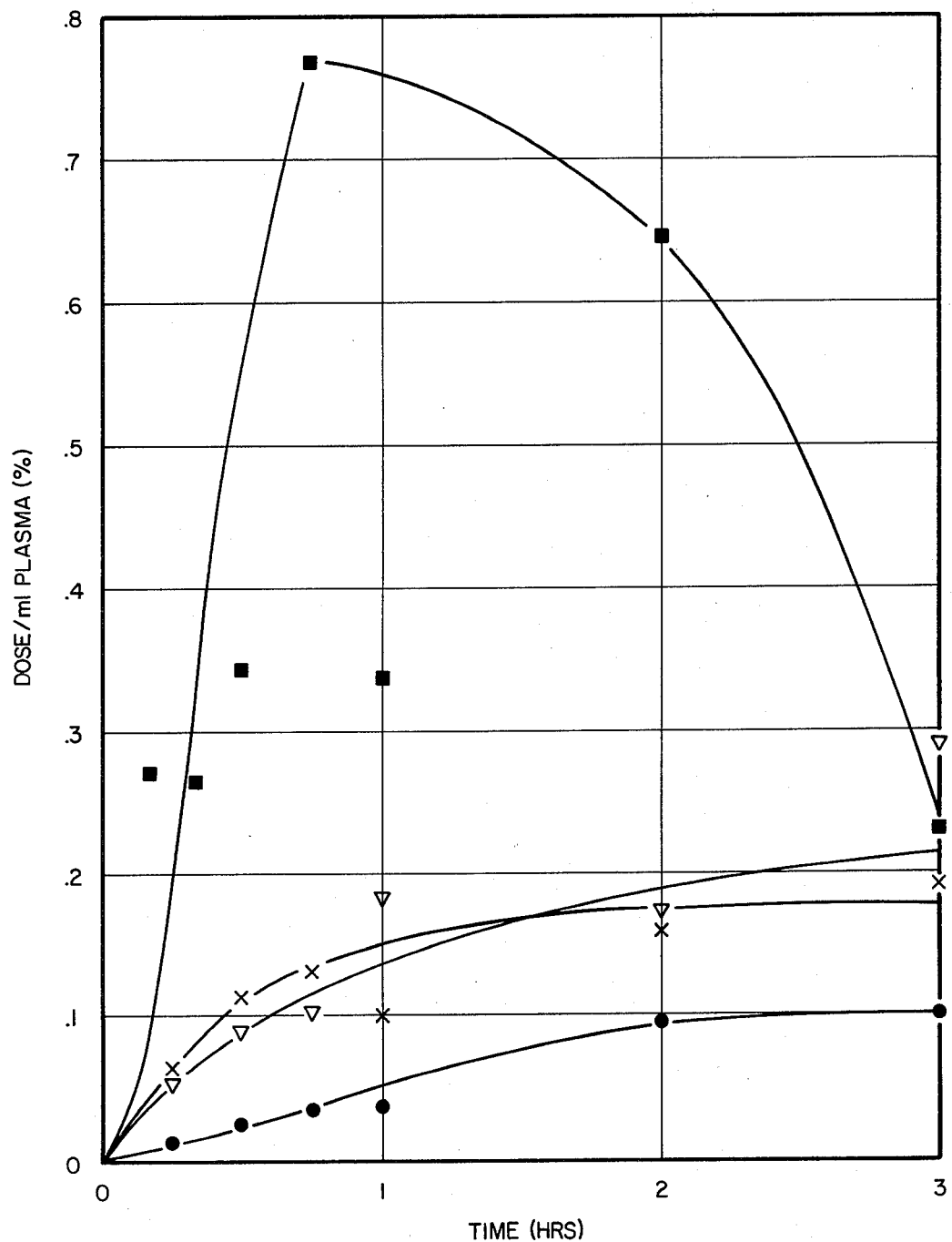
FIG_1

PROSTAGLANDIN COMPOSITIONS

This is a continuation of application Ser. No. 075,912 filed July 16, 1979, now abandoned.

BACKGROUND OF THE INVENTION

1. Field of the Invention

This invention relates to a parenterally administratable composition containing a 16-phenoxy prostaglandin and polyethylene glycol having a molecular weight from 380 to about 630 which is useful as an abortifacient.

2. Prior Art

The compounds which are useful in the composition of this invention are disclosed and described in U.S. Pat. No. 3,985,791, issued Oct. 12, 1976 to Muchowski and Fried. It is also known that certain prostaglandins, for example, PGE$_1$, PGE$_2$, PGA$_2$ or the 15-keto, 15-methyl, 15-hydroxy or 3-oxa derivatives, possess tranquilizing activity and can be mixed with polyethylene glycol 400 and powdered polyethylene glycol 6000 to give orally administratable lozenges.

Prostaglandins are often unstable, and several solutions to solving this stability problem have been proposed. See for example 4,011,313 to Thompson which relates to a stabilized prostaglandin composition which employs a dialkylated mono- or polyalkylene glycol. It is also known that the prostaglandin PGE$_1$ can be made into a topical cream suitable for the treatment of psoriasis by mixing with polyethylene glycol 400, a polyethylene glycol 4000 and 1,2,6-hexanetriol.

We have now discovered that dl-9α,11α,15α-trihydroxy-16-phenoxy-17,18,20-tetranorprosta-4,5,13-trans-trieneoic acid and the lower alkyl esters of 1 to 4 carbon atoms thereof, when mixed with a polyethylene glycol having a molecular weight of 380 to about 630, can be subcutaneously injected into a mammal and exhibits release rate much lower than would be expected and thus allows for prolonged activity of the prostaglandin.

SUMMARY AND DESCRIPTION OF PREFERRED EMBODIMENTS

The broadest aspect of the present invention is a composition consisting of a polyethylene glycol having a molecular weight of 380–630, a 16-phenoxy-prostaglandin represented by the formula

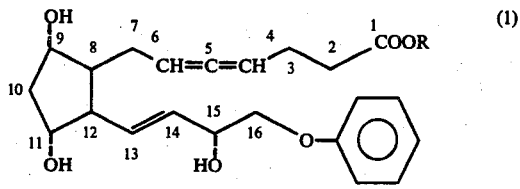

(1)

wherein R is hydrogen or a lower alkyl group of 1 to 4 carbon atoms and optionally other suitable pharmaceutical excipients. The compounds useful in the composition of this invention are fully described in U.S. Pat. No. 3,985,791 and that patent is incorporated herein by reference.

Another aspect of the invention is a process for producing a luteolytic effect in a female mammal by parenterally administering the above composition to said mammal.

The dotted lines shown in the above formula indicate that the substituents are in the alpha configuration, i.e. below the plane of the cyclopentane ring. The double bond at C-13 in the compounds useful in the present invention has the same configuration as that in natural prostaglandins of the PGE and PGF type series, that is the trans configuration. These prostaglandin compounds possess asymmetric centers and thus can be produced and used as racemic mixtures or as individual 8 R-antimers. Racemic mixtures can be resolved if desired at appropriate stages by methods known to those skilled in the art, to obtain the respective individual antimers. It is to be understood that the racemic mixtures and the individual 8 R-antimers are encompassed within the compounds which are useful in the composition and method of this invention.

The term "lower alkyl" as used herein, unless otherwise specified, refers to straight or branched alkyl groups containing up to 4 carbon atoms, e.g. methyl, ethyl, n-propyl, isopropyl, n-butyl, t-butyl and the like.

The polyethylene glycols (hereinafter sometimes referred to as PEG) which are useful in the composition and method of this invention include liquid polymers of the general formula H(OCH$_2$CH$_2$) OH having a molecular weight of about 380 to 630 where n has a value of between about 8 and 14. Exemplary products include PEG 400 where n is between 8.2–9.1 and has a molecular weight range of 380–420 and PEG 600 where n is between 12.5–13.9 and has a molecular weight range 570–630. PEG 400 is preferred.

The instant composition can be prepared either alone or in combination with other pharmaceutically compatible excipients which aid in maintaining the stability or purity of the composition. For example, the composition can optionally contain small amounts of preservatives, antioxidants and/or pH buffering agents. Suitable preservatives which can be used include, for example, benzyl alcohol and the like. Suitable buffering agents include, for example, citric acid, ascorbic acid, triethanolamine and the like. Suitable antioxidants include, for example, ascorbic acid and dl-α-tocopherol.

In addition the composition can also contain up to about 20% by weight water. Preferrably, however, the composition contains less than about 5% by weight water and most preferably is substantially anhydrous, i.e., less than 0.5% water.

Generally the composition will contain about 0.001% to 5.0% by weight (preferably 0.025% to 0.1%) of the active ingredient, less than 1.0% by weight (preferably 0.001% to 0.1%) of the pharmaceutical excipients and the remainder, i.e., about 94.0% to 99.9% by weight (preferably 98.0% to 99.9%) of the polyethylene glycol.

The compositions of this invention are administered parenterally, i.e. introduced by way other than the intestine. This includes subcutaneous and intramuscular administration. The compounds used in the compositions of this invention are typically administered in dosages of about from 0.0002 to 0.2 mg. per Kg. of body weight. The precise effective dosage will, of course, vary depending upon the mode of administration, condition being treated and host.

The compositions of the present invention exhibit prostaglandin-like biological activities and thus are useful in the treatment of mammals where the use of prostaglandins is indicated. Particularly, these compositions have luteolytic activity, i.e., the compositions produce luteolysis with resulting abortion and thus are abortifacient compositions. The compositions are further useful for controlling the reproductive cycle in female mammals and for inducing estrus and regulating ovulation in female animals such as horse, cow and swine. They are also useful for inducing labor in pregnancy and for inducing menses in human females, to correct or reduce menstrual abnormalities. Preferably the use is producing abortion in feed lot animals.

The effect of vehicle viscosity on parenteral drug absorption has been studied previously. See Kiichiro Katemi et al, Chem. Pharm. Bull., 20, 443 (1972). Generally it is found that the higher the viscosity, the slower the rate of release of the active ingredient.

The unique aspect of the compositions of this invention is that release (and thus absorption) of the specific prostaglandin compounds defined above is much slower than would be expected from the vehicle viscosity effect taught in the prior art.

This unexpectedly great decrease in absorption rate can be seen by comparing the absorption data of a drug from glycerin versus that of the same drug from PEG 400. Glycerin has a greater viscosity than PEG 400 and thus would be expected to give a lower rate of absorption than the PEG 400 composition. However, glycerin demonstrates a greater absorption rate, just the opposite of what is expected. The absorption rate of the composition of this invention is less than the absorption rate of glycerin with 10% water even though the viscosity of the glycerin/water mixture is still greater than the viscosity of the PEG 400. Thus, it appears that the results could not be predicted from the prior art.

The value of the lower release rate and prolonged absorption of the prostaglandin lies in the resultant increase in biologic activity of the compound administered. This is due in part to short plasma half-life of the prostaglandin compounds. The decrease in absorption rate with resultant increase in the overall drug absorption time results in a longer duration of effective plasma concentration of the drug. The decreased absorption rate also eliminates the toxic or unwanted side effects from the prostaglandin compounds.

EXAMPLE 1

This example sets forth the process for preparing the injectable solution.

Two and a half grams (g) of the prostaglandin of Formula (I) wherein R is hydrogen, 2.5 g ascorbic acid (antioxidant) and 45 g benzyl alcohol (preservative) are dissolved with stirring in the PEG 400 vehicle to prepare 5.0 liters of the composition. The resulting solution is then sterile filtered through a 0.4 micron membrane filter. The sterile solution is then aseptically sterile filled into sterile vials and sealed.

EXAMPLE 2

A series of experiments was carried out to determine the absorption rate of a compound which are useful in the composition of this invention as compared to other compositions which are not included within the scope of the claims of the invention. In each experiment 56 rats were used. Two groups of 27 rats are required for the test formulations and the two remaining rats are used to obtain blank plasma samples. Each animal is injected subcutaneously (SQ) or intramuscularly (IM) as indicated in the Table with 0.15 ml of the appropriate composition. Each composition is prepared by dissolving 2.7 milligrams of the compound in 10 milliliters of the solvent. This represents approximately 5 microcuries of carbon 14 and 41 micrograms of dl-9$\alpha$,1-1$\alpha$,15$\alpha$-trihydroxy-16-phenoxy-17,18,19,20-tetranorprosta-4,5,13-trans-trienoic acid (Compound A). Blood samples from each of three rats from each group are obtained by cardinal puncture at the following time points after injection: 15 minutes, 30 minutes, 45 minutes, 60 minutes, 2 hours, 3 hours, 4 hours, 5 hours and 6 hours. The two untreated rats are sampled to obtain blank plasma sample. The results are summarized in Table 1 and in FIG. 1.

TABLE I

| Comp. | Vehicle | Route | Viscosity (cp) 25° C. | Viscosity (cp) 37° C. | Injected Vol (ml) | Amount Injected ($\mu$Ci) | Relative Percent Absorption* | Absorption Rate Constant Ka(hr$^1$) |
|---|---|---|---|---|---|---|---|---|
| A | Aq. Buffer | (IM) | 1.05 | .736 | .15 | 5 | 100 | 10.14 |
| A | Aq. Buffer | (SQ) | 1.05 | .736 | .15 | 5 | 60.9 | 10.14 |
| A | Glycerin | (SQ) | 895.00 | 358.00 | .15 | 5 | 50.4 | 5.0 |
| A | 90% Glycerin H$_2$O | (SQ) | 213.4 | 99.70 | .15 | 5 | 51.5 | 6.5 |
| A | PEG 400 | (SQ) | 91.42 | 52.29 | .15 | 5 | 27.6 | 3.7 |
| A | PEG 400 | (IM) | 91.42 | 52.29 | .15 | 5 | 35.5 | 3.7 |
| A | PEG 400 | (SQ) | 91.42 | 52.29 | .30 | 10 | 26.2 | 3.7 |
| A | PEG 400 | (SQ) | 91.42 | 52.29 | .15 | 5 | 31.4 | 3.7 |

*Compared to aqueous buffer over 6 hours.

From the results of this experiment it is clear that the composition from which the active material was absorbed at the slowest rate when administered subcutaneously was the composition of the invention, namely polyethylene glycol 400 and the active ingredient. Even though glycerin and 90% glycerin had a viscosity greater than polyethylene glycol and therefore would be expected to exhibit a release rate and therefore a rate of absorption lower than that of polyethylene glycol, this was not found to be true. FIG. (I) graphically points this out.

The subject matter claimed is:

1. An injectable composition containing less than 5% by weight water for producing a luteolytic effect in a mammal which comprises polyethylene glycol having a molecular weight of 380 to about 630; a luteolytic effective amount of a compound chosen from those represented by the formula

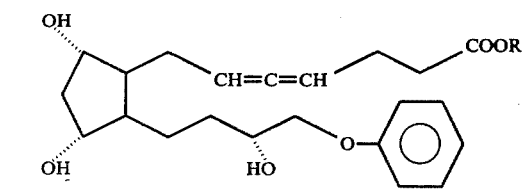

wherein R is hydrogen or alkyl of 1 through 4 carbon atoms; and optionally a phrmaceutically acceptable excipient, said composition exhibiting a prolonged absorption of said compound by said mammal.

2. The composition of claim 1 wherein R is hydrogen and said polyethylene glycol has a molecular weight of about 380 to 420.

3. The composition of claim 1 wherein R is methyl and said polyethylene glycol has a molecular weight of about 380 to 420.

4. A method for producing a prolonged luteolytic effect in a mammal which method comprises parenterally administering the composition of claim 1 to said mammal.

5. The method of claim 4 wherein R is hydrogen and said polyethylene glycol has a molecular weight of about 380 to 420.

6. The method of claim 4 wherein R is methyl and said polyethylene glycol has a molecular weight of about 380 to 420.

* * * * *